(12) United States Patent
Remacle et al.

(10) Patent No.: US 8,247,196 B2
(45) Date of Patent: Aug. 21, 2012

(54) REAL-TIME PCR OF TARGETS ON A MICRO-ARRAY

(75) Inventors: Jose Remacle, Malonne (BE); Isabelle Alexandre, Namur (BE); Sylvain Margaine, Namur (BE); Dieter Husar, Namur (DE)

(73) Assignee: Eppendorf Array Technologies S.A., Namur (BE)

( * ) Notice: Subject to any disclaimer, the term of this patent is extended or adjusted under 35 U.S.C. 154(b) by 460 days.

(21) Appl. No.: 11/719,582

(22) PCT Filed: Nov. 18, 2005

(86) PCT No.: PCT/EP2005/012383
§ 371 (c)(1),
(2), (4) Date: Feb. 16, 2009

(87) PCT Pub. No.: WO2006/053770
PCT Pub. Date: May 26, 2006

(65) Prior Publication Data
US 2009/0156415 A1 Jun. 18, 2009

Related U.S. Application Data

(63) Continuation-in-part of application No. 10/991,087, filed on Nov. 18, 2004.

(30) Foreign Application Priority Data

Nov. 18, 2004 (EP) .................................. 04027435

(51) Int. Cl.
*C12P 19/34* (2006.01)
(52) U.S. Cl. ..................................................... 435/91.2
(58) Field of Classification Search .............. 435/6, 91.2
See application file for complete search history.

(56) References Cited

U.S. PATENT DOCUMENTS

| 6,280,945 B1 * | 8/2001 | U'ren | 435/6 |
| 2004/0253714 A1 * | 12/2004 | Trulson et al. | 435/287.2 |
| 2005/0064488 A1 * | 3/2005 | Huh et al. | 435/6 |

FOREIGN PATENT DOCUMENTS

WO  WO 2005/118773 A2  12/2005

OTHER PUBLICATIONS

Liu et al. 2002 "DNA Amplification and Hybridization Assays in Integrated Plastic monolithic Devices" *Analytical Chemistry* 74(13): 3063-3070.
Liu et al. 2003 "Self-contained, integrated biochip systems for sample-to-answer genetic assays" *7th Conference on Miniaturized Chemical and Biochemical Analysis Systems* pp. 1319-1322.
Liu et al. 2004 "Self-contained, fully Integrated biochip for sample preparation, polymerase chain reaction amplification, and DNA microarray detection" *Analytical Chemistry* 76(7):1824-1831.
Mitterer et al. 2004 "Microarray-based identification of bacteria in clinical samples by solid-phase PCR amplification of 23S ribosomal DNA sequences" *Journal of Clinical Microbiology* 42(3):1048-1057.
Northup 1998 "A miniature analytical instrument for nucleic acids based on micromachined silicon reaction chambers" *Analytical Chemistry* 70(5): 918-922.
Wang et al. 2004 "Identification and characterization of *Bacillus anthracis* by multiplex PCR on DNA chip" *Biosensors & Bioelectronics* 20(4):807-813.

* cited by examiner

*Primary Examiner* — Gary Benzion
*Assistant Examiner* — Cynthia Wilder
(74) *Attorney, Agent, or Firm* — Knobbe Martens Olson & Bear LLP

(57) ABSTRACT

The present invention relates to a method and apparatus for monitoring on a micro-array a PCR amplification of a nucleotide molecule being present in a solution. The method includes the steps of: providing a support having fixed upon its surface a microarray having at least a capture molecule being immobilized in specifically localized areas of the support and a reaction chamber; introducing a solution containing the nucleotide molecule into the reaction chamber and reagents for nucleotide molecule amplification and labelling; submitting the solution to at least 2 thermal cycles having at least 2 and preferably 3 different temperature steps in order to obtain labelled target nucleotide molecule by PCR amplification; performing at least a measurement of the labelled target nucleotide molecule in at least one thermal cycle by incubating the labelled target nucleotide molecule under conditions allowing a specific binding between the target nucleotide molecule and its corresponding capture molecule and measuring the light emission from the bound labelled target nucleotide molecule in response to excitation light with the solution being present in the chamber and containing the labelled target nucleotide molecule. The surface of emission for a localized area is between about 0.1 µm$^2$ and about 75 mm$^2$. The method further includes processing the data obtained in at least one thermal cycle in order to detect and/or quantify the amount of nucleotide molecule present in the solution before the amplification.

31 Claims, 4 Drawing Sheets

REAL-TIME PCR OF TARGETS ON A MICRO-ARRAY

A Sequence Listing submitted as an ASCII text file via EFS-Web is hereby incorporated by reference in accordance with 35 U.S.C. §1.52(e). The name of the ASCII text file for the Sequence Listing is SEQUENCE.TXT, the date of creation of the ASCII text file is Feb. 23, 2012, and the size of the ASCII text file is 1.62 KB.

FIELD OF THE INVENTION

The present invention relates to a method and an apparatus and diagnostic kit for monitoring a polymerase chain reaction (PCR) for nucleic acid amplification over multiple thermal cycles on capture molecules fixed on a micro-array. More particularly, the invention allows the detection and quantification of nucleotide molecule in a real time PCR amplification using micro-arrays. The invention also comprises means and apparatus for performing the method.

DESCRIPTION OF THE RELATED ART

The disclosed nucleotide molecule detection method offers the advantages of speed, simplicity and multiplexing over prior methods for detecting amplified nucleic acids. Nucleic acid detection techniques in general are very useful in medical diagnostic assays.

The sensitivity and specificity of nucleic acid detection methods was greatly improved by the invention of the polymerase chain reaction (PCR). PCR is a process for amplifying nucleic acids and involves the use of two oligonucleotide primers, an agent for polymerization, a target nucleic acid template, and successive cycles of denaturation of nucleic acid and annealing and extension of the primers to produce a large number of copies of a particular nucleic acid segment. With this method, segments of single copy genomic DNA can be amplified more than 10 million fold with very high specificity and fidelity. Methods for detecting PCR products are described in U.S. Pat. No. 4,683,195. Those methods require an oligonucleotide probe capable of hybridizing with the amplified target nucleic acid. These methods require separate steps of amplification, capture, and detection and generally require several hours to complete.

Due to the enormous amplification possible with the PCR process, small levels of DNA carryover from samples with high DNA content, positive control templates, or from previous amplifications, can result in PCR product even in the absence of purposefully added template DNA. Because the possibility of introducing contaminating DNA to a sample will be increased as the amount of handling steps required for sample preparation, processing, and analysis is increased, it would be preferable to minimize sample handling for their detection and quantification, particularly after the amplification reaction is complete.

Methods for simultaneous amplification and detection of target nucleic acids have been described in order to minimize the problems of sample contamination. The U.S. Pat. Nos. 4,683,195 and 6,171,785 involve the introduction of detectable DNA binding agents (such as ethidium bromide) into the amplification reaction, which agents produce a detectable signal that is enhanced upon binding double-stranded DNA. An increased in fluorescence of the PCR mixture indicates that amplification has occurred. The U.S. Pat. Nos. 6,395,518 and 5,952,202 discloses an oligonucleotide probe including a fluorescer molecule attached to a first end of the oligonucleotide and a quencher molecule attached to the opposite end of the oligonucleotide such that the fluorescer is substantially unquenched whenever the oligonucleotide probe is in a double-stranded state. A DNA polymerase having 5' to 3' nuclease activity digests said probes during amplification to separate the reporter dye from the quencher. An increased in fluorescence of the PCR mixture indicates that amplification has occurred. The U.S. Pat. No. 5,716,784 provides an alternative method based on the use of two complementary probes, the first analytical probe being labelled at its 5' terminus with an energy transfer donor fluorophore, and the second detection probe being labelled at its 3' terminus with an energy transfer acceptor fluorophore. Measurement of oligonucleotide analytical probe hybridized in solution to oligonucleotide detection probe measured spectrophotometrically in solution by energy transfer measurement, provides a measure of the amount of oligonucleotide analytical probe used up in the amplification of the target nucleic acid sequence and thus provides a measure of amount of target nucleic acid sequence amplified in the PCR replication procedure. The U.S. Pat. No. 5,928,907 describes an apparatus for monitoring the formation of a nucleic acid amplification reaction product in real time which uses a fiber optic focused in the volume of the sample.

Although those methods are capable of monitoring in real time the quantification of nucleic acids in an homogeneous PCR hybridization system, they are limited to the quantification of one target nucleic acid per fluorescent dye. The multiplexing is not easy to implement due to the requirement of non overlapping fluorescent dyes for measuring the increase in signal related to the amplification of several target nucleic acids in the same apparatus.

A problem underlying the present invention resides in providing an improved method for monitoring a PCR in real-time in heterogeneous system, obviating the shortcomings associated with prior art methods. Specifically, the method should be simple to carry out and cost effective.

The present invention aims to overcome most of these limitations by proposing a simple and effective method and apparatus for the simultaneous amplification of multiple target molecules on a micro-array.

SUMMARY OF THE INVENTION

In order to realize the above-mentioned objectives, the method for monitoring on a microarray a PCR amplification of a nucleotide molecule being present in a solution comprises the steps of:

providing a support (15) having fixed upon its surface a micro-array comprising at least a capture molecule (20) being immobilized in specifically localized areas (21) of said support and a reaction chamber (14), introducing a solution containing said nucleotide molecule into said reaction chamber (14) and reagents for nucleotide molecule amplification and labelling, submitted the solution to at least 2 thermal cycles having at least 2 and preferably 3 different temperature steps in order to obtain labelled target nucleotide molecule (13) by PCR amplification, performing at least a measurement of the labelled target nucleotide molecule in at least one thermal cycle in the following way, incubating said labelled target nucleotide molecule (13) under conditions allowing a specific binding between said target nucleotide molecule (13) and its corresponding capture molecule (20), measuring the light emission (7) from the bound labelled target nucleotide molecule in response to excitation light (2) with said solution being present in the chamber and containing the labelled target nucleotide molecule (13), wherein the surface of emission for a localized area is comprised between about 0.1 µm² and about 75 mm², and Processing the data obtained in at least one thermal cycle in order to detect and/or quantify the amount of nucleotide molecule present in the solution before the amplification.

The apparatus for monitoring on a micro-array a PCR amplification of a nucleotide molecule being present in a solution according to the present invention comprises:

a support (15) having fixed upon its surface a micro-array, comprising at least one capture molecule (20) being immobilized in specifically localized areas (21) of said support, which is in fluid communication in a chamber with said nucleotide molecule and reagents for nucleotide molecule amplification and labelling, a thermal cycler for carrying out an automated PCR process, said thermal cycler capable of alternately heating and cooling said support for producing labelled target nucleotide molecule, an excitation light source (1), a detector (10) for measuring the electromagnetic light emission (7) from the bound labelled target nucleotide molecule in response to said excitation light with said solution being present in the chamber and containing the labelled target nucleotide molecule wherein the surface of emission for a localized area is comprised between about 0.1 µm² and about 75 mm², wherein the different parts are integrated into the same apparatus in order to read the light emission of the bound labelled target nucleotide molecule during the PCR amplification.

The apparatus further comprises:

a storage system for storing the data of the different measurements for at least 5 localized areas of the support at a defined timing of a thermal cycle, a controller (11) repeating the steps of excitation, detection and storage at least one time in at least one thermal cycle for each localized area of the micro-array, a program for processing the data obtained in at least one thermal cycle in order to detect and/or quantify the amount of nucleotide molecule present in the sample before the amplification.

The invention also comprises a diagnostic kit for monitoring on a micro-array a PCR amplification of a nucleotide molecule being present in a solution comprising:

a support (15) having fixed upon its surface a micro-array, comprising at least one capture molecule (20) being immobilized in specifically localized areas (21) of said support wherein the surface of said support is maintained flat at temperature higher than 85° C. and wherein said support have a low self-fluorescence, a reaction chamber comprising 2 or even better 3 parts being in fluid connection to each other comprising a flat surface carrying the micro-array.

DETAILED DESCRIPTION OF THE INVENTION

Definitions

Figure 1:
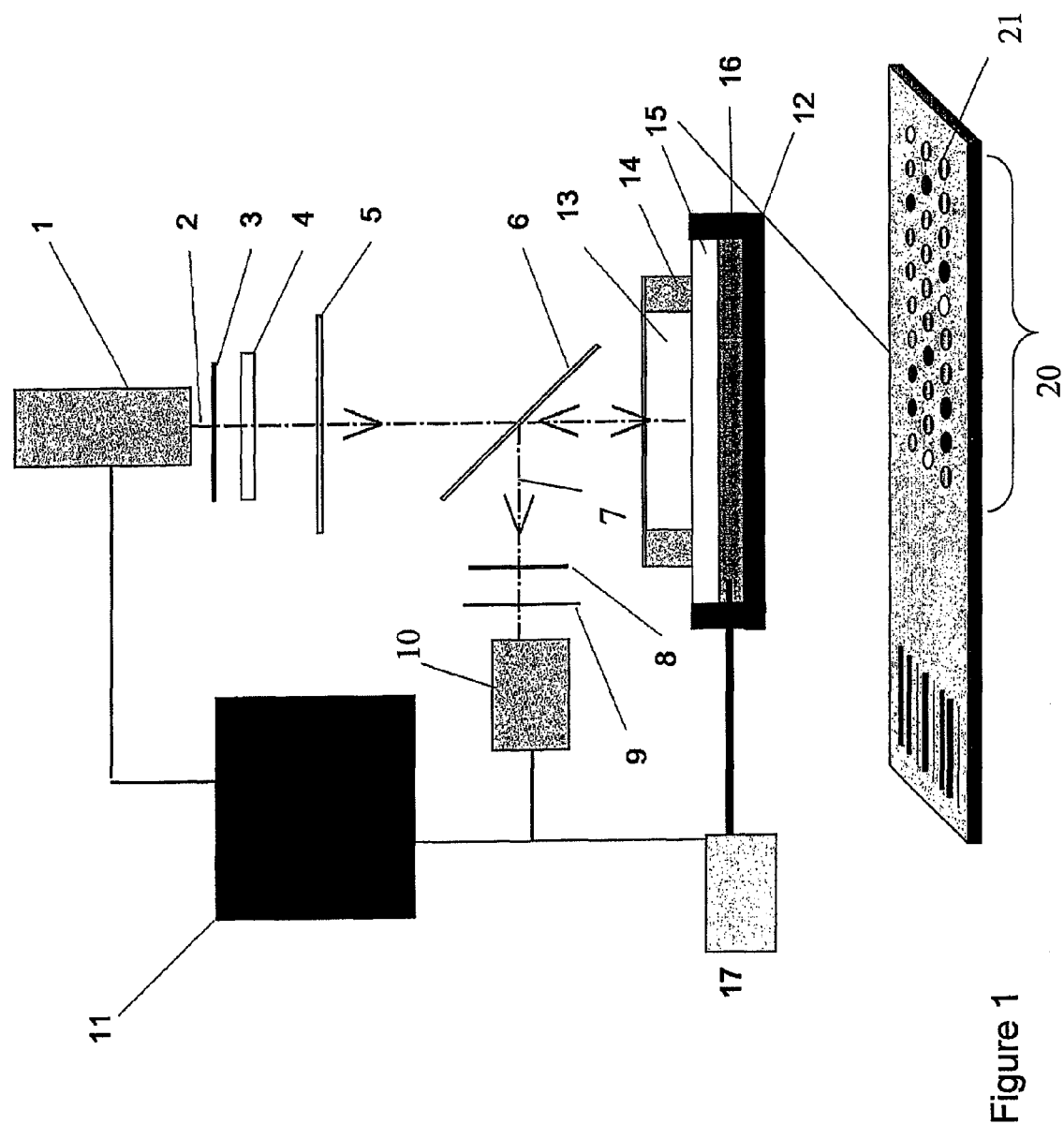
FIG. 1. General scheme of the integrated apparatus comprising the support (15) a carrier (12), temperature regulating device (16) and a temperature controlling device (17) and the detector (10).

In the context of the present application and invention the following definitions apply:

As used herein, "capture molecule" refers to a molecule, or complex or combination thereof, that is capable of specifically binding to one target molecule, or to a family of target molecules, or to one or more member (s) of a plurality of target molecules, or portion(s) thereof. The capture molecules are preferably nucleic acids, which are either synthesized chemically in situ on the surface of the support or laid down thereon. Nucleic acid binding is achieved via base pairing between two polynucleotides, one being the immobilized capture molecule and the other one the target to be detected. Capture molecule also comprises derivative of the nucleic acid such as PNA or LNA as long as they can bind specifically the target polynucleotide molecule.

The term "single capture probe species" is a composition of related polynucleotides for the detection of a given sequence by base pairing hybridization or by molecular recognition between polypeptides or proteins. Polynucleotides are synthesized either chemically or enzymatically or purified from samples but the synthesis or purification is not always perfect and the capture molecule is contaminated by other related molecules like shorter polynucleotides. The essential characteristic of one capture species for the invention is that the overall species can be used for capture of a given target nucleotide molecule.

The term "directly on the surface of the support" means that the main part of the light beam is directed on the surface of the support and excites itself the fluorescence molecules being present on the surface.

The terms "nucleic acid, micro-array, probe, target nucleic acid, bind substantially, hybridizing specifically to, background, quantifying" are as described in the international patent application WO97/27317, which is incorporated herein by way of reference.

The term "nucleotide triphosphate" also called dNTP refers to nucleotides present in either as DNA or RNA and thus includes nucleotides, which incorporate adenine, cytosine, guanine, thymine and uracil as bases, the sugar moieties being deoxyribose or ribose. Other modified bases capable of base pairing with one of the conventional bases adenine, cytosine, guanine, thymine and uracil may be employed. Such modified bases include for example 8-azaguanine and hypoxanthine.

The term "nucleotide" as used herein refers to nucleosides present in nucleic acids (either DNA or RNA) compared with the bases of said nucleic acid, and includes nucleotides comprising usual or modified bases as above described.

References to nucleotide(s), polynucleotide(s) and the like include analogous species wherein the sugar-phosphate backbone is modified and/or replaced, provided that its hybridization properties are not destroyed. By way of example the backbone may be replaced by an equivalent synthetic peptide, called Peptide Nucleic Acid (PNA).

The term "polynucleotide" sequences that are complementary to one or more genes or to the genome sequence described herein, refers to polynucleotides that are capable of hybridizing under stringent conditions to at least part of the nucleotide sequence of said genes or genome or copy thereof. Polynucleotides also include oligonucleotides being of more than 2 bases but below 100 bases long which can be used under particular conditions. Such hybridizable polynucleotides will typically exhibit at least about 75% sequence identity at the nucleotide level to said genes or genome, preferably about 80% or 95% sequence identity or preferably more than 95% nucleotide sequence identity to said genes or genome. They are composed of either small sequences typically 15-30 base long or longer ones being between 30 and 100 or even longer between 100 and 800 base long depending on the specificity and sensitivity requirements for the assay.

The term "homology" is intended to mean the degree of identity of one polynucleotide sequence to another polynucleotide sequence. There may be complete homology (i.e. 100% identity) between two or more polynucleotides. The degree of homology is calculated after alignment of the sequence and may be determined by any methods well known for a person skilled in the art.

"Micro-array" means a support on which multiple capture molecules are immobilized in order to be able to bind to the given specific target molecule. The micro-array is preferentially composed of capture molecules present at specifically localized areas on the surface or within the support or on the substrate covering the support. A specifically localized area is the area of the surface which contains bound capture molecules specific for a determined target molecule. The specific localized area is either known by the method of building the micro-array or is defined during or after the detection. A spot is the area where specific target molecules are fixed on their capture molecules and seen by the detector. A spot is the area where specific target molecules are fixed on their capture molecules and seen by the detector. In one particular application of this invention, micro-arrays of capture molecules are also provided on different supports as long as the different supports contain specific capture molecules and may be distinguished from each other in order to be able to quantify the specific target molecules. This can be achieved by using a mixture of beads having particular features and being able to be recognized from each other in order to quantify the bound molecules. One bead or a population of beads are then considered as a spot having a capture molecule specific of one target molecule.

The terms "background" or "background signal intensity" refers to hybridization signals resulting from non-specific binding, or other non specific interactions, between the labelled target nucleic acids and components of the polynucleotide micro-array (e.g. the polynucleotide probes, control probes, the micro-array substrate, etc.). Background signals may also be produced by intrinsic fluorescence of the micro-array components themselves. A single background signal can be calculated for the entire micro-array, or different background signals may be calculated for each target nucleic acid. In a preferred embodiment, the background is calculated individually for each spot, being the level intensity of the signal on the surface surrounding the spot and not bearing the specific capture molecule.

The nucleotide molecules of the invention are typically detected by detecting one or more "labels" attached to the nucleotide molecule. The labels may be incorporated by any of a number of means well known to those of skill in the art, such as detailed in WO 99/32660, which is incorporated herein by way of reference. The label is detected directly preferably in fluorescence.

The nucleotide molecule is intended to mean a polynucleotide present in the biological material of interest and to be detected. They are obtained either after extraction or purification of the molecules of interest present in a sample being preferentially a biological material. The term "biological material", includes within its meaning organisms, organs, tissues, cells or biological material produced by a cell culture.

Advantageously, the measurement of the target nucleotide molecules is performed on a solid phase in the presence of labelled amplified target molecules being present in the solution. The method avoids removing the solution from the surface of the support carrying a micro-array and avoids washing before the measurement. The washing includes liquid handling of the solution containing amplified target and possible contamination of further assays in the laboratories.

Advantageously, the method of the invention does not require the use different fluorescent dyes to quantify different nucleotide molecules. One fluorescent dye is sufficient for the quantification of multiple different nucleotide molecules because of their specific binding by hybridization on capture molecules being specific of each target nucleotide sequence and being localized in distinct areas of the micro-array. For example, a nucleotide molecule is amplified together with another nucleotide molecule using the same or different primers and both amplicons are labelled with the same fluorescent dye. The different amplicons are detected and/or quantified on separated capture molecules without the need of several fluorescent dyes as required in the real time solution PCR.

Another advantage of the method is its great specificity. A first specificity level is obtained through the annealing of the primers and a second level of specificity is obtained by the hybridization on the capture molecules. Such double specificity increases very much the specificity of the final detection which is often required for analysis in complex biological sample. Another advantage is that primer dimers or non specific amplified product formed during the PCR amplification will not generate signal on the micro-array since there is no complementary capture molecules for the primers nor for unspecific products.

The specificity can still be increased by the use of different capture molecules for the same target nucleotide molecule. Two or more capture molecules can be designed to bind the same strand or one capture probe will bind the sense strand of the amplified product and another capture molecule the antisense strand.

Advantageously, the nucleotide molecules to be amplified are homologous nucleotide sequences which are quantified on micro-array during the PCR using consensus primers as described in WO0177372. The same primers are used to amplify all the homologous sequences possibly present in a sample. The amplicons which are labelled with the same fluorescent dye are discriminated on different capture molecules, each one targeting a different homologous sequence. So with only one primer pair and one fluorescent dye, the assay is rendered multiplex by the use of multiple capture probes present on the micro-array. In one embodiment the number of sequences amplified by the same primer pair is higher than 2 and even higher than 5 and even higher than 20. The amplified targets are then detected on the array.

In another embodiment, standards nucleotide sequences are incorporated into the tested solution and the standards are amplified with the same primers as the target nucleotide sequences.

In still another embodiment, the

In the main embodiment, target and/or capture molecules are polynucleotides. The capture molecules are attached preferably by covalent link on the support or substrate present on the support. In another embodiment, the capture molecules are adsorbed on the support as long as they are not significantly released in solution during the PCR cycles.

Deposition of the capture probe is preferentially done with physical means such as pin or "pin and ring" touching the surface, or by release of a micro-droplet of solution by methods such as piezo or nanodispenser. Alternatively, in situ synthesis of capture molecules is one of the invention embodiment with light spacial resolution of the synthesis of oligonucleotides or polynucleotides in known locations such as provided by U.S. Pat. No. 5,744,305 and U.S. Pat. No. 6,346,413.

In another embodiment the nucleotide molecules are DNA present in a biological sample. The DNA is extracted from the sample and amplified by PCR and the amplicons are detected online by their fixation on their specific capture molecules. In one particular embodiment, the nucleotide molecules are homologous nucleotide sequences which are detected and/or quantified online on micro-array after amplification of genomic DNA by consensus primers as described in WO0177372.

According to the invention, the solid support for the micro-array is preferably selected from the group consisting of glass, metallic supports, polymeric supports (preferably thermo-resistant having low self-fluorescence) or any other support used in the microchips (or micro-arrays) technology (preferably activated glass bearing aldehyde or epoxide or acrylate groups), said support comprising also specific coatings, markers or devices (bar codes, electronic devices, etc.) for improving the assay.

In a preferred embodiment, the support (15) contains a substrate on which are fixed the capture molecules.

If glass presents many advantages (like being inert and having a low self-fluorescence), other supports like polymers, with various chemically well-defined groups at their surface, allowing the binding of the nucleotide sequences are useful. In another preferred embodiment, the support bearing the capture molecules has a 3 dimensional porous structure. Conventional glass slides have less than 60% silicon dioxide on their surface. This inherently limits the amount of chemical bonding available on the surface. Porous material exhibits increased loading capacity of capture molecules. Typical porous supports are gel pads, fused-fiber matrix, fibrous polymer matrix. The array can be constructed entirely of the porous material, or can comprise a layer of porous material mounted on top of a flat surface such as glass, plastic, or metal.

In another embodiment capture molecules are present on different supports being preferentially beads with chemical or physical characteristics for their identification with a specific capture molecule.

In still another embodiment, the support bears several micro-arrays separated by physical or chemical boundaries. Examples for physical barriers are wells, e.g. the support being a 96, 384, 1536 multi-well plate, thus creating separated localized areas onto which capture molecules may be spotted individually. 384-well and 1536-well plates are available from BD Falcon for cell based assays (Merck Eurolab sa, Leuven, Belgium) or from Nunc A/S (Roskilde, Denmark). 6144 format microtiter plates are available from Parallel Synthesis Technologies Inc. (PSTI, Menlo Park, Calif., USA). The multiwells are present as one plate or in strips. Other physical barriers are tubes such as 96, 384, 1536 or even 6144 tubes deposit at the surface of the support. Tubes are similar to the well formats but do not have a plain bottom so that when deposit on the surface of the support, they create localized areas isolated from each other. An example for a chemical barrier is e.g. described in DE 0019949735A1, where defined areas within a hydrophobic surface are provided with hydrophilic anchors allowing the precise location and confinement of capture molecules on a solid support.

In a preferred embodiment, the support bears several micro-arrays separated by physical boundaries, preferably in a multi-well plate or strip format. In another embodiment, the multiwell plate is submitted to a temperature gradient during the measurement of light emission (7).

In a preferred embodiment, the reaction chamber contains 2 or even better 3 parts being in fluid connection to each other comprising a flat surface carrying the micro-array. The support is preferably made of a plastic slide covered with a flow through observation channel where the micro-array is build up. The observation channel is terminated by one or two reservoirs preferably located at both sides. One reservoir is preferably used to introduce the solution and the other one to remove it. The reservoirs are sealed by specific lids to avoid the evaporation of the solution during thermal cycles. In a particular embodiment, the solution is moved over the micro-array in order to increase the speed of the binding reaction of the labelled target nucleotide molecule on its capture molecule. This is obtained by rotating, translating or moving up and down the reaction chamber during at least the annealing step of the thermal cycle. In still another embodiment, the height of the liquid on the surface having fixed the micro-array is lower than 1 mm and preferably lower than 0.1 mm and even more preferably lower than 0.02 mm.

In the preferred embodiment, the polynucleotides being used as capture molecule are between 10 and 1000 nucleotide long and preferably between 100 and 400 nucleotides long. For specific binding of homologous sequences possibly present in the same sample, the polynucleotide capture molecules contain a spacer according to the patent WO0177372. Specific binding of homologous sequences or SNP possibly present in the same sample, are obtained using capture molecules having a specific part being between 10 and 30 nucleotides.

In the preferred embodiment, the polynucleotides being used as capture molecules are present on the micro-array localized area at a density superior to 10 fmoles, and preferably 100 fmoles per $cm^2$ surface of the solid support.

The micro-array according to this invention contains between 4 and 100000 spots per $cm^2$ and preferably between 20 and 1000 spots per $cm^2$, each spot being the localized area for one capture molecule. Miniaturization allows performing one assay onto a surface (usually circular spots of about 0.1 to about 1 mm diameter). A low density array, containing 20 to 400 spots is easily obtained with pins of 0.25 mm at low cost. Higher density of spots going to 1,600 spots per cm2 can be obtained by reducing the size of the spots for example to 0.15 mm. Method for obtaining capture molecules of higher density have been described earlier as in U.S. Pat. No. 5,445,934. Miniaturization of the spot size allows obtaining a high number of data which can be obtained and analyzed simultaneously, the possibility to perform replicates and the small amount of biological sample necessary for the assay. Miniaturization for detection on micro-arrays is preferably associated with microfluidic substrate for separation, extraction of nucleotide molecules from the cell extract.

In a preferred embodiment, the micro-array comprises more than 5 different capture molecules (20), preferably more than 20 and even more than 50.

In a preferred embodiment, the localized area is comprised between about 10 $\mu m^2$ and about 1 $mm^2$ and preferably between about 1 $\mu m^2$ and about 100 $\mu m^2$.

In one preferred embodiment, the capture molecules present on the micro-array are complementary to at least one part of the sequence of amplified target nucleotide sequence present in solution. The capture molecules comprise a nucleotide sequence which is able to specifically bind the amplified target nucleotide sequence, said specific nucleotide sequence is also preferably separated from the surface of the solid support by a spacer arm of at least about 6.8 nm or 20 nucleotides in a double stranded form which has no binding affinity for the amplified target molecule. In a preferred embodiment, the capture molecule is a single stranded polynucleotide containing a sequence able to specifically bind the labelled target nucleotide molecule and a spacer of at least 20 nucleotides and better more than 90 nucleotides. The spacer part can be either single or double stranded DNA.

In a preferred embodiment the probe sequence specific for the target binding is comprised between 15 and 100 nucleotides and more preferably between 15 and 35 nucleotides Detectable labels suitable for use in the present invention include any composition detectable by electromagnetic light emission. In an embodiment, the target molecules are labelled with a fluorescent dye. The fluorescent label can be incorporated into the target by enzymatic or chemical reaction. Typical enzyme reaction includes the incorporation of nucleotide analogues into the target. Alternatively, primers labelled at their 5' end with a fluorescent dye can be incorporated into the target. Fluorochromes can also be incorporated into the targets by chemical reaction such as the reaction of fluorescent dye bearing a N-hydroxysuccinimide (NHS) group with amines groups of the targets. Useful fluorescent dyes in the present invention include cyanine dyes (Cy3, Cy5, Cy7), fluorescein, texas red, rhodamine, green fluorescent protein. Preferably, the excitation wavelength for cyanin 3 is comprised between 540 and 558 nm with a peak at 550 nm and the emission wavelength is comprised between 562 and 580 nm with a peak at 570 nm.

Preferably, the excitation wavelength for cyanin 5 is comprised between 639 and 659 nm with a peak at 649 nm and the emission wavelength is comprised between 665 and 685 nm with a peak at 670 nm. Preferably, the excitation wavelength for cyanin 7 is comprised between 733 and 753 nm with a peak at 743 nm and the emission wavelength is comprised between 757 and 777 nm with a peak at 767 nm.

Patents teaching the use of such labels include U.S. Pat. Nos. 3,817,837; 3,850,752; 3,939,350; 3,996,345; 4,277,437; 4,275,149; and 4,366,241. In a preferred embodiment, the fluorescent dye is cyanin 3, cyanin 5 or cyanin 7.

Some fluorescent labels may be of particular interest, such as nanocrystals particles having fluorescent properties. The most common one are the Quantum dots (Han et al., Nature Biotechnology 19, 631-635, 2001). They are fluorescent and do not bleach with time or with illumination. Their stability makes them particularly suitable for the use in continuous reading as proposed in this invention. Also, they contain metals which confer to these particles specific properties so that other methods than the fluorescence can be used to follow their attachment on the capture probes. Thermal heating of these particles is one of the parameters that may be followed with time. The fact that the metal absorbed the energy of a light beams preferably a laser and induce a heating of the particle has been used as a basis for the detection of low density gold particle on a support and even single particles are detected (Boyer et al Science, 297, 1160-2002). The method is called Photothermal Interference contrast.

Another technology for the direct measurement of nanoparticles is the Rayleigh Scattering. This method is based on the use of a light beam adapted in order to obtain an oscillation of the electrons in the metal particle so that an electromagnetic radiation is obtain from the particle which can be detected. (Stimpson et al., Proc. Natl. Acad. Sci. USA 100 (2003), 11350-11353) (real-time detection of DNA hybridization and melting on oligonucleotide arrays by using optical wave guides) The method is lacking sensitivity for the applications on biological samples.

Alternatively, Raman scattering and the surface plasmon resonance may be applied in the present invention, which technique has been extensively used for the detection of antibody/antigen binding but are also well suited for the multiparametric measurement of the arrays and for the required sensitivity on biological samples. (Thiel et al., Analytical Chemistry, 69 (1997), 4948-4956).

In another embodiment, quartz crystal microbalances may be applied, which are now sensitive enough that they can measure changes of mass lower than nanogram (cf. Caruso et al., Analytical Chemistry 69 (1997), 2043-2049). This is one proposal for micro-array detection in real-time.

Cantilevers are another option for the detection of DNA on micro-arrays. (McKendry et al. Proc. Natl. Acad. Sci. USA, 99 (2002), 9783-9788).

Also, another technology is the electrical detection of the nanoparticles which takes into account their metal properties. The electrochemical detection was first applied but with low sensitivity. The more advanced and sensitive method is the detection by differential pulse voltametry (Ozsoz et al., Analytical Chemistry 75 (2003), 2181-2197).

The resistivity and the capacitance properties of the metal are also one of the best properties to be detected on electronic chips. The presence of a metal between two electrodes will induce a change of resistivity and of capacitance. The detection of the DNA or proteins is then observed when the capture molecules are present on one of the electrode (Moreno-Hagelsieb et al Sensors and Actuators B-Chemical, 98, 269-274, 2004). The capacitance assay of the gold labelled DNA has been described by Guiducci et al. ESSDERC 2OO2. Since electronic chips can be made of several plots, different targets may be detected on different plots and the change in the resistivity or in the capacitance may be recorded. If the methods have not yet been able to produce reliable and sensitive detections as required by the biological samples, it is, however, predicted that some of them will succeed to fulfil the requirements for the realtime detection.

Another promising technology for measuring the binding of the target molecules on capture molecule of the microarray is the chemical cartography based on optical process of non-linear generation frequency spectroscopy (GFS) (L. Dreesen et al. Chem Phys Chem, 5, 1719-1725, 2004). This technology allows the imaging in real time of the vibrational properties of surfaces and interfaces with a submicron spacial resolution. The measurement is obtained by mixing at the surface of a substrate two laser beams, one having a fixed frequency in the visible (green) and the other having a variable frequency in infrared. The vibrational signature at the interface is obtained by measuring the light emitted by the sample in function of the frequency of the infrared laser beam. This method allows to avoid labelling of the target in order to be detected.

The original nucleotide molecule is not necessary labelled before the amplification but lead to amplified labelled target molecules during the amplification step.

Figure 4:
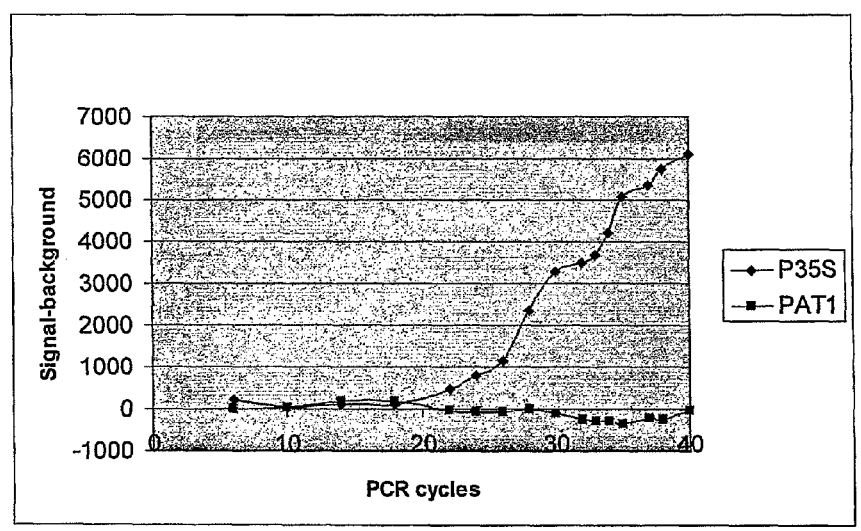
FIG. 4. Results for the online detection of PCR amplification on micro-array using labelled primer as schematically represented in FIG. 2. PCR is performed on a GMO inserted sequence in the presence of a micro-array comprising different bound capture molecules, with one being specific of the amplified product (P35S) and the other one (PAT1) not. Measurements are performed during the annealing step of different thermal cycles on P35S and PAT1 capture molecules.

The amplified nucleotide molecules are able to hybridize on the capture molecules after a denaturation step. As the amplified nucleotide molecules are double stranded, in theory they must reassociate in solution much faster than to hybridise on capture molecules fixed on a solid support where diffusion is low and the specific binding sequence is short, thus reducing even more the rate of reaction. Therefore, it was unexpected to observe a significant signal increase on the capture molecules over multiple thermal cycles after a short period of incubation time (FIG. 4).

In a particular embodiment the measurement is performed on bound target labelled molecules while they reassociate in a double stranded form in the solution during annealing and/or elongation of the thermal cycle.

In a preferred embodiment, the reagents for nucleotide molecule amplification comprise a primer pair, dNTPs, a thermostable DNA polymerase and buffer.

In a particular embodiment, the assay is performed in a continuous or semi-continuous way over the annealing and/or elongation and/or denaturation step.

In a preferred embodiment, the reagents for nucleotide molecule amplification comprise a primer and/or dNTP labelled with a fluorescent dye, preferably Cyanin 3, Cyanin 5 or Cyanin 7.

In a specific embodiment, two or more fluorescent dyes are used in the same solution. In an alternative embodiment, the solution composition is adapted for performing the annealing of the primers on the nucleotide molecule and the specific binding of the labelled target molecule on the capture molecule during the same temperature step.

In a preferred embodiment, the thermostable DNA polymerase used for PCR on micro-array is the hot Master (Eppendorf, Hamburg, Germany) which works at 62° C. In a preferred embodiment the steps of annealing, elongation and hybridization on the array are performed at the same temperature which is comprised between 60 and 68° C. Advantageously, the method of the invention is compatible with most of the thermostable DNA polymerase available on the market. It does not necessary require a 5' to 3' nuclease activity as described in the U.S. Pat. No. 5,952,202.

Figure 2:
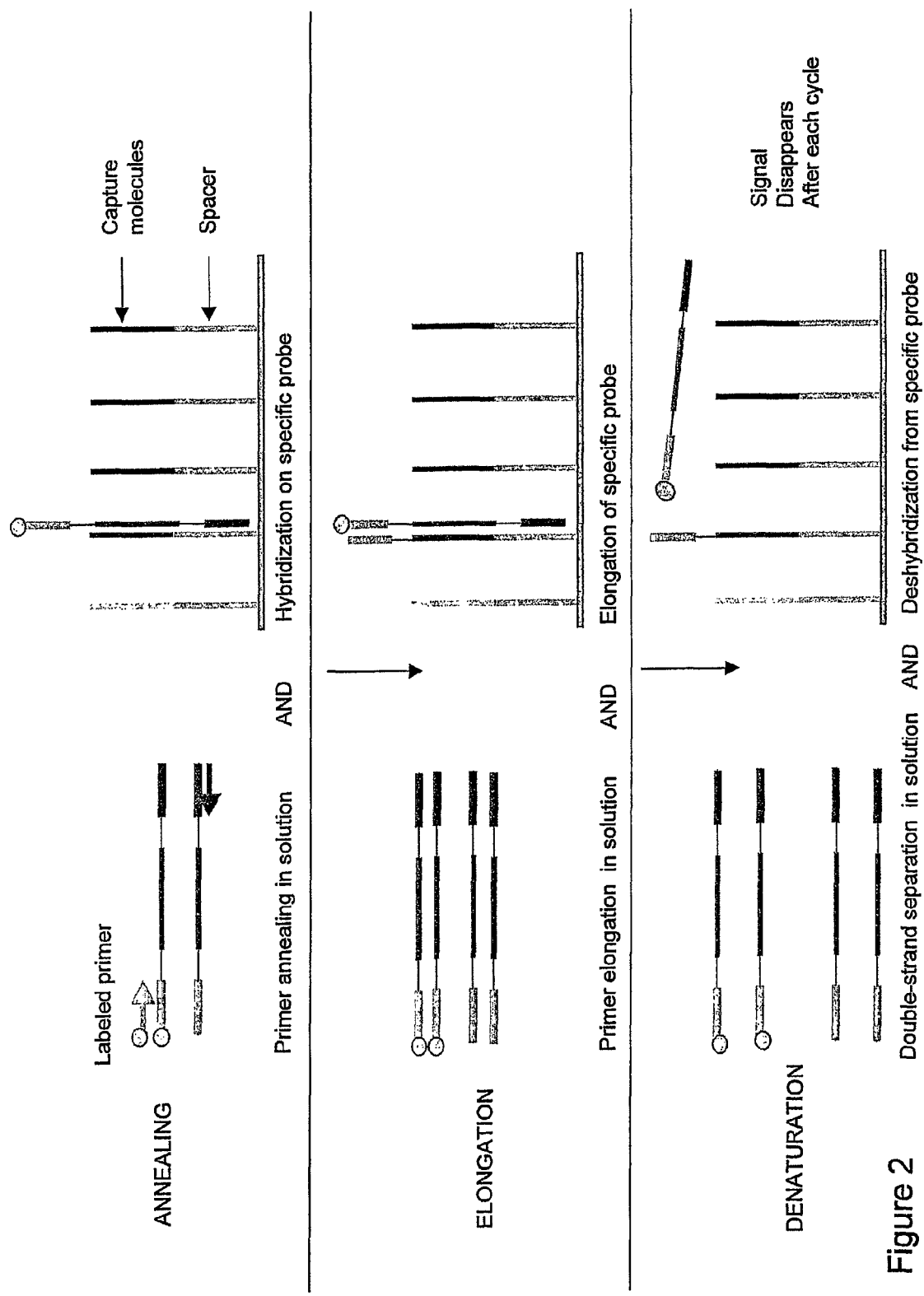
FIG. 2. Schematic description of the online detection of PCR product on micro-array using labelled primer. PCR is performed in the presence of a micro-array comprising different capture molecules. Alternate steps of annealing, elongation and denaturation during one cycle of reaction result in the accumulation of labelled products which hybridize on their capture molecule present on the micro-array but deshybrizes from their specific capture molecules after each denaturation cycle.

In an embodiment, the solution contains 5' end labelled oligonucleotides or primers which serve as anchors for the polymerase to copy the target sequences to be detected on the micro-array. FIG. 2 shows the detection of PCR product on micro-array using labelled primer. Unexpectedly, during the temperature step of annealing of a thermal cycle, the primers hybridize with the nucleotide molecule in solution while the amplified target molecule obtained in a previous thermal cycle hybridize in the same time and in the same conditions, on a capture molecule being immobilized in a specifically localized area of a support. During the temperature step of elongation of a thermal cycle, the primers hybridized to the nucleotide molecule are elongated in solution. The capture molecules (20) bound to the labelled target nucleotide molecules are possibly elongated but not labelled. Alternate steps of annealing, elongation and denaturation during one cycle of reaction result in the accumulation of labelled products which hybridize on their capture molecule present on the micro-array but deshybrizes from their specific capture molecules after each denaturation cycle.

In a preferred embodiment, the labelled target nucleotide molecules are specifically bound on their corresponding capture molecules (20) preferably during the temperature step of annealing and/or elongation.

In another embodiment, the solution contains labelled dNTP which are incorporated by the polymerase into the target sequences to be detected on the micro-array.

Figure 3:
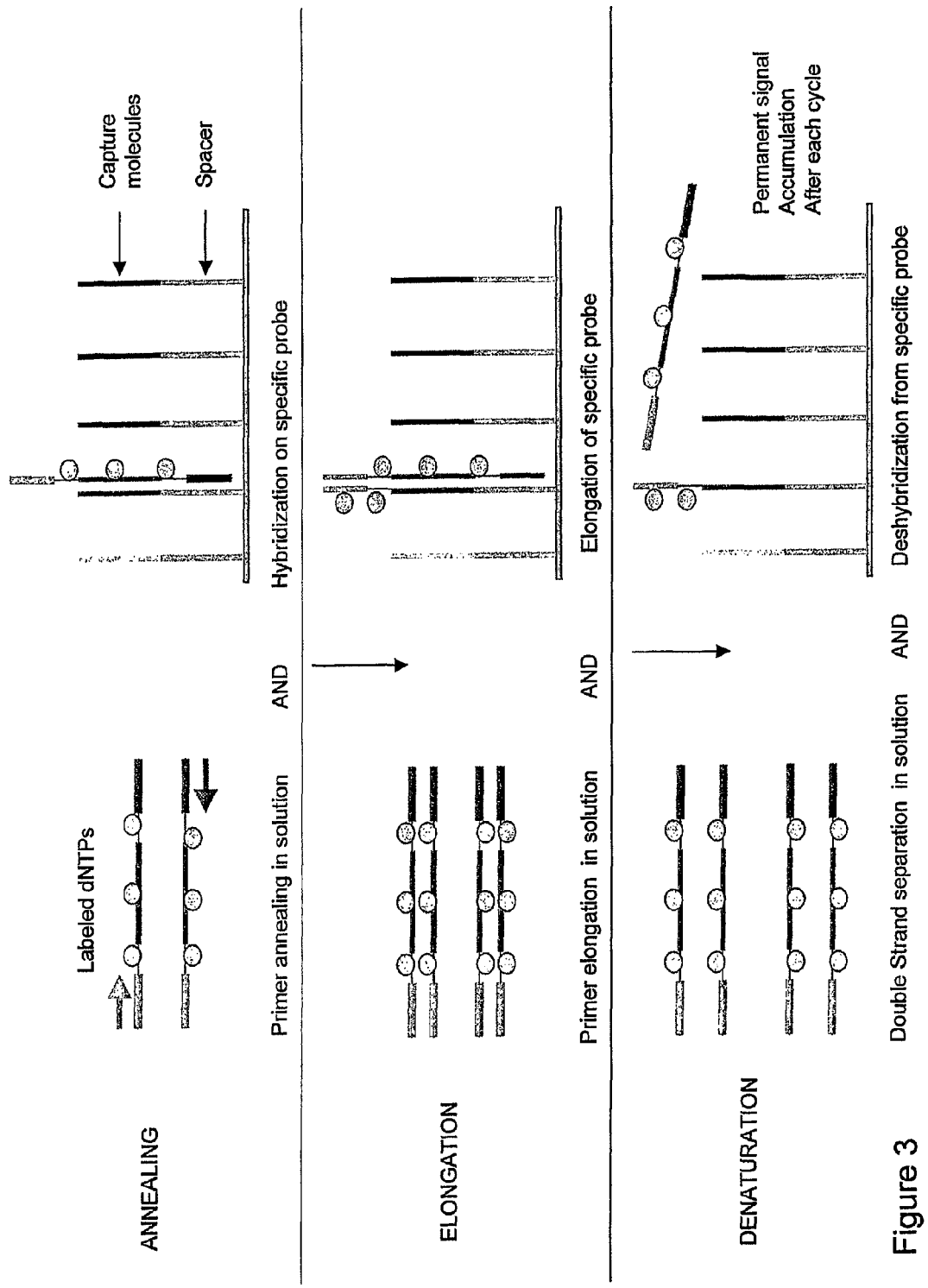
FIG. 3. Schematic description of the online detection of PCR product on micro-array using labelled dNTPs. PCR is performed in the presence of a micro-array comprising different capture molecules. Alternate steps of annealing, elongation and denaturation during one cycle of reaction result in the accumulation of labelled product which is partly integrated into its specific capture molecule after each denaturation cycle and detected.

FIG. 3 shows the detection of PCR product on micro-array using labelled dNTPs. During the temperature step of annealing of a thermal cycle, the primers hybridize with the nucleotide molecule in solution while the amplified target molecule obtained in a previous thermal cycle hybridize in the same time and in the same conditions, on a capture molecule being immobilized in a specifically localized area of a support.

During the temperature step of elongation of a thermal cycle, the primers hybridized to the nucleotide molecule are elongated in solution while, the immobilized capture molecules (20) having bound to the target nucleotide molecules are elongated and labelled. Alternate steps of annealing, elongation and denaturation during reaction cycles result in the accumulation of labelled product being partly integrated into its specific capture molecule and which can be detected during or at the end of each of the denaturation step.

In an embodiment, some capture molecules are elongated by the polymerase and some are in the same time hybridized with the amplified products which accumulate in solution during the thermal cycle. In one embodiment, the capture molecules elongated are detected during the temperature step of denaturation. In another embodiment, the capture molecules elongated and the labelled nucleotide molecules bound on their capture molecule are both detected during the temperature step of annealing and/or elongation.

In a preferred embodiment, the hybridization is favoured over the elongation by using capture probes which are not capable of being elongated. In this case, capture molecules preferably include a base terminator or long stretch of identical bases at their 3' end such as polyA. Alternatively, the capture molecules are immobilized on the support by their 3' end, the free 5' end being not able to be elongated by the polymerase.

In another embodiment, the elongation is favoured over the hybridization by performing PCR in the presence of one primer in excess and a reduced amount of the other primer.

In another embodiment, at the end of the thermal cycles, an annealing step of at least 10 min, and better at least 30 min and even better at least 60 min is performed in order to increase the signal of hybridization for nucleotide molecules present at a very low concentration before the amplification.

In a preferred embodiment, a thermal cycle is performed within 10 min and better within 6 min and even better within 3 min. In an alternative embodiment, 30 thermal cycles are performed within 5 h and better within 3 h and even better within 1.5 h.

Advantageously, the length of the amplified target nucleotide molecules are selected as being of a limited length preferably between 100 and 800 bases, preferably between 100 and 400 bases and more preferably between 100 and 200 bases. This preferred requirement depends on the possibility to find primers to amplify the required sequences possibly present in the sample. Too long target may reallocate faster and adopt secondary structures which can inhibit the fixation on the capture nucleotide sequences.

The thermal cycler is preferably composed in its simplest version of the following relevant components:
a thermocouple, a transmitter, a converter and a heater.

The thermocouple, sticks as close as possible of the localized area of the micro-array to heat, measures the temperature thought the transmitter. This temperature information is given to a computer via the converter. Every 0.1 second, the software compares the real temperature measured to the temperature set point requested by the final user. If the measured temperature is higher than the requested one, the heater is simply stopped (no active cooling). If the measured temperature is lower than the set point, the system continues the heating process. The thermal cycler is preferably adapted to fit the support format being preferably a microscopic slide of about 2.5×7.5 cm or a 96 wells microtiter plate. The alternative heating and cooling is preferably obtained using a peltier or pulsed air.

In a preferred embodiment, the thermal cycler is capable of alternatively heating and cooling the support at a ramping of 5° C. per min, preferably 10° C. per min and better 30° C. per min and ever better 40° C. per min.

The method is particularly well fitted to control the light excitation since the light is directed on the surface of the support and the homogeneity of the excitation at each localized area can be determined and corrected if necessary In a preferred embodiment, the light beam is a laser beam which is focused on the surface of the micro-array in order to excite directly the fluorescent molecules. The laser beam is preferably focused perpendicular to the surface of the array either through the solution or through the support. The emitted light is detected in the opposite direction of the excitation laser beam. The emitted light is preferably detected as a confocal light and measure after amplification by a photomultiplier. In the preferred embodiment the surface of the microarray is scanned by the laser beam in order to obtain a maximum light excitation of the bound targets.

In a preferred embodiment, the excitation light (2) from a light source (1) is directed on the surface of the support.

In a preferred embodiment, the signal associated with a capture molecule on the micro-array is quantified. The preferred method is the scanning of the array(s) with a scanner being preferentially a laser confocal scanner for the detection of fluorescent labelled targets. The resolution of the image is comprised between 1 and 500 μm and preferably between 5 and 50 μm.

In a preferred embodiment, a measurement of the labelled target nucleotide molecule is performed in at least 5, preferably at least 10 thermal cycles and even preferably at least 20 thermal cycles.

In a preferred embodiment, the light emission (7) is measured at a defined timing from the beginning of a temperature step, for example after 1 min of annealing.

In another preferred embodiment, the light emission (7) is measured at within 5 min and even within 2 min and even better within 1 min after the beginning of the annealing temperature step. In an alternative embodiment, the light emission (7) is measured at the end of at least one of the 3 temperature steps used for the PCR amplification.

In still another embodiment, the light emission (7) is measured at the end of the PCR amplification.

The micro-array is preferably scanned and each localized area is subsequently measured. Preferably the scanning of the array is performed within 1 min and better within 30 sec and even better within 10 sec. Preferably the scan of each localized areas is measured at the same precise moment of a temperature step when reading is repeated over multiple thermal cycles, The fact that each localized area is subsequently measured can be advantageously used to monitor a kinetic of hybridization of a labelled target nucleotide molecule on the same capture probe which has been immobilized at different localized areas of the support and which are scanned in a time dependant manner. Since the temperature is maintained constant during the measurement, the target nucleotide molecule continues to hybridize on their capture probe during the scanning.

In a particular embodiment, the data on the quantification of the amplified target molecules performed at different PCR cycles are processed in order to quantify the amount of nucleotide molecule present in the original solution before the amplification. The amplification cycles lead to the doubling of the target sequence in each cycle when the efficiency of the amplification is maximal. Quantification of the original nucleotide concentration is calculated from the extrapolation of the first cycle which gives a detectable value or a value crossing a fixed threshold. The concentration is then calculated from a reference curve or from the data obtained on a standard molecule.

In a preferred embodiment, the data are processed in order to obtain a signal value for each of the localized area. In another embodiment, the data are processed in order to obtain a signal value for each of the localized area and for the local background. The data are further processed by subtracting the background from the signal value for each of the localized area. In a preferred embodiment, the quantification of the amount of nucleotide molecule is performed by comparing the signal value of the localized area with a fixed value.

In an alternative embodiment, the quantification of the amount of nucleotide molecule is performed by comparing the number of thermal cycles necessary to reach a fixed value (cycle threshold or CT) with the CT of a reference nucleotide molecule. The reference nucleotide molecule is preferably amplified in the same solution and detected on the same micro-array as the target nucleotide molecule.

In another embodiment, the quantification of the amount of nucleotide molecule is performed by comparing the number of thermal cycles necessary to reach a fixed value (CT) with a standard curve wherein the CTs are plotted against standard concentrations.

In an embodiment, the micro-array is in contact with reagents for carrying out the amplification of one or more nucleotide sequences. In a preferred embodiment, between 1 and 4 nucleotide molecules and better between 1 and 20 nucleotide molecules present in a solution are amplified and detected and/or quantified in the same assay. In another embodiment, between 20 and 1000 nucleotide molecules present in a solution are amplified and detected and/or quantified in the same assay.

The apparatus used in order to perform the method according to the invention contains two different parts.

The first one contains the incubation system which provides the conditions necessary for the binding reaction of the targets onto their capture molecules. Preferably the first part contains a temperature control system for regulating and controlling the temperature during the binding reaction.

In a preferred embodiment, the temperature regulating device is selected from the group consisting of a controlled peltier, a micro-thin wire heating element laid in a pattern between optical grade polyester sheets like Thermal-Clear™ transparent heaters from Minco, or fluidic system circulating externally temperature regulated fluid.

In a preferred embodiment, the temperature regulating device is mounted on a carrier holding the support. The temperature regulating device is preferably positioned between the carrier and the support.

In another embodiment, the temperature regulating device is mounted on the support and is not in contact with the carrier.

In a preferred embodiment, the incubation system provides conditions so that the thickness of the solution being in contact with the micro-array is constant above all the arrayed spots or localized areas. The difference of thickness between two spots or localized areas of the arrayed surface is preferably lower than 100 micrometers and even lower than 10 micrometers and even lower than 1 micrometer.

In another embodiment, the incubation system provides conditions for the thickness of the solution being in contact with the micro-array is changed between two measurements.

The first part of the apparatus also preferably contains a mixing or agitation system for the liquid to be moved inside the reaction chamber and increase the reaction rate. In a preferred embodiment, the mixing is performed by movement of the liquid by physical means such as pump, opening and closing valves, electrostatic waves or piezoelectric vibrations.

The second part contains the detection system required to detect the light emission from the target bound to their corresponding capture molecules. A light source generates a beam of light to excite the labeled targets on the support. In the preferred embodiment, the detection part has to be settled in such a way as to obtain the same detection efficiency on the overall surface covered by the micro-array to be analyzed.

In a preferred embodiment, the excitation light is a laser beam preferably having a wavelength of about 532 nm delivered at a power of about 15 mW with a divergence that may be below 1.2 mrad. In another embodiment, the detection system contains 2 or even 4 lasers.

In a preferred embodiment, the laser beam (2) generated by the light source (1) is nearly collimated and nearly Gaussian. An exchangeable excitation filter (4) is used to collect only the wavelengths of interest. An additional filter wheel (3) is preferably placed and used as an attenuation filter to precisely regulate the laser power. This filter wheel is shaded differently at variable know absorption levels. A lens (5) that may be anti-reflection coated is used for focusing the laser beam on the support (15). The distance between the light source, the lens and the support is variable to allow focusing.

Thereafter, the light passes through a dichroic mirror or beam splitter (6). This mirror pass light having a wavelength lower than about 530 nm, but reflect light having a wavelength greater than 560 nm. Consequently, the 532 nm light coming from the laser is passed through the dichroic mirror to the support. The light then passes through a reaction chamber (14) and the fluorescent marked sample (13) and reaches the support (15), where bound labeled target are excited and emit fluorescence at about 560 nm.

Emitted light (7) is then focused through a focusing lens (9) to a photomultiplier tube (10) for detecting the number of photons present therein.

In a specific embodiment, an additional emission filter (8) that transmits light having a wavelength greater than about 550 nm is added. Thus, photomultiplier tube (10) detects substantially only fluoresced light. The Photomultiplier tube generates a pulse for each photon detected. Each of these pulses is amplified and converted to an electronic signal by photoelectric effect. A data acquisition board or controller (11) then collects the resulting signals. The controller includes a temperature controlling device for controlling the temperature steps needed for PCR amplification.

After data are collected from a region of the substrate, the carrier (12) moves the support so that excitation light is directed to a different region on the support (15). The process is repeated until all regions on the substrate have been scanned. In another embodiment the support is fixed and the light excitation beam is moved from one part to the other on the surface of the support. In still another embodiment, the overall micro-array is illuminated and the light emission from each localized area is detected.

In one embodiment, the support itself is a carrier. In a preferred embodiment, the data are stored and treated for calculation of the amount or concentration of the different target molecules in solution and in the original biological sample. Data storage and data treatment are preferably performed using a programmable computer which is integrated in the apparatus of the invention. Data treatment can be performed at any time after data storage.

In one embodiment, the support is moved relative to the detection system during the reading. The support moves relative to the excitation light to allow the reading of different regions of the support. The excitation light may be fixed or moved in one direction to scan the support.

In an alternative embodiment, the support is moved relative to both the incubation and detection systems. During the incubation, the support is in contact with the temperature control system (incubation position). When a reading has to be effected, the support is moved from the incubation system to the detection system (reading position). During the reading, the support is either moved relative to the excitation light or is fixed. After the reading the support turns back to its initial position. One advantage of moving the support relative to the incubation part during the reading is to avoid deleterious effect of the heating device on parts of the detection system.

In another embodiment, the two parts of the apparatus are fixed and work together with no movement of the solid support relative to the incubation and detection parts. A typical detector used in this context is a CCD camera capable to take a picture of the whole micro-array.

In a specific embodiment the apparatus is controlled by a programmable computer which controls the parameters of the two parts of the system. The scanner is comparable to a Genepix 4200A scanner from Axon coupled with the scriptable Genepix 5.1 software from Axon.

At STEP 1, the user is prompted to fill in the required parameters, such as: resolution, voltage of the PMT, laser power, number of scans, time between scan, scan area. Temperature of the substrate is set separately on the heating system that can be a peltier device mounted on the substrate. Parameters of the System:

The resolution defines the pixel size. Generally, the pixel size is chosen which results in more than 1 pixel per localized area and preferably between 10 and 100. Setting a too high resolution generates an overload of data while having a too low pixel size generates low quality results. The PMT voltage multiplies the detected signal. Increasing the laser power will increase the photon count in each pixel.

The "number of scan" parameter corresponds to the number of times the user wishes to scan the substrate while the "time between scans" parameter controls the amount of time to wait before commencing a subsequent scan. In this manner, the user may perform a series of scans to follow the kinetics of the reaction.

Scan area parameter corresponds to the size of the substrate to be tested. The temperature parameters control the temperature at which detection is performed. Temperature may vary depending on the type of polymers being tested. Preferably, testing is done at a temperature that produces maximum binding affinity while minimizing mismatches.

The system is then initialized: carrier is moved to home position while laser power is checked. At STEP 2, first scan is performed and the fluorescence emitted on the selected region comprising the micro-array of the substrate is collected. The JavaScript callback is launched when the scan is done (STEP 3). If the number of scans to be done is not reached, then the program waits for the delay asked by the user. Then the image is saved at STEP 4, and if required a new scan is performed (STEP 5). The JavaScript callback allows the loop to be continued. In STEP 6, values are extracted from the data and in STEP 7; the calculation and analysis are performed. For this purpose a grid which contains the number of rows and columns of the micro-array to be measured is positioned on the micro-array. The grid is composed of circles which diameter in pixels correspond to the diameter of the spots to be quantified. The diameter is depending on the resolution chosen for the scanning. The means of the pixels intensity inside the circle gives the spot signal. This signal is then calculated for each time and plotted versus the incubation time. STEP 6 is preferably performed by importing the scanned 16-bit images to the software, 'ImaGene4.0' (Bio-Discovery, Los Angeles, Calif., USA), which is used to quantify the signal intensities.

Algorithm

```
<html>
<head>
    <style type="text/css">
        @import url(GenePix_Style_Base.css);
    </style>
    <title>Example Automation</title>
</head>
<body marginheight="0" marginwidth="0" topmargin="0" leftmargin="0">
<!-- HTML Layout portion -->
<p>
<table width=600 border=0 cellspacing=0 cellpadding=5>
    <tr class="title">
        <td>
            <p class="heavy">Real-time scanning: allow scanning multiple time the same sample at
constant time intervals without any user intervention
        </td>
    </tr>                                   // STEP 1: USER PARAMETERS
    <tr>
        <td class="underline instructions">
            <p>PMT: <input type=text size=2 name=setpmt value="700">
            <p>Résolution: <input type=text size=2 name=setres value="40"> μm
            <p>Scan interval: <input type=text size=2 name=interval value="120"> (s)
            <p>Scan numbers: <input type=text size=2 name=snumber value="10">
<p>
<input type=checkbox size=5 name=saved value="10">Save images ?
            <p>Images directory: C:\Documents and Settings\user\desktop\<input type=text size=20
name=ipath value="">
        </td>
    </tr>
    <tr>
        <td class="underline instructions">
            <input type="button" value="Prescan" onclick="GenePix.PreviewScan( )">
            <input type="button" value="Start scanning" onclick="startscan( )">
        </td>
    </tr>
    </tr>
</table>
<!-- Scripting portion -->
<script language=vbscript>
//
++++++++++++++++++++++++++++++++++++++++++++++++++++++++++++++++++++++++
+++++++++++++++++++++++++++++++++++++++++++++++++++++++++
Option Explicit
Dim GenePix
Dim Scanner
dim i            // PMT VALUE
dim j            // RESOLUTION (μm)
dim k            // SCAN INTERVAL (s)
dim n            // NUMBER OF SCANS
dim c            // COUNTER
dim s            // IMAGES PATH
dim t1           // TIMER
// This procedure is launched by pressing on the start scan button
++++++++++++++++++++++++++++++++++++++++++++++++++++++++++++++++++++++++
+++++++++++++++++++++++++++++++++++++++++++++++++++++++++
sub startscan( )                            // STEP 2
c=0
Set GenePix = window.external              // declares scanner object
Set Scanner = GenePix.Scanner
GenePix.DiscardImages( )                   // clears the display
call InitializeCallbacks( )                //   defines the Javascript callbacks
i=cint(setpmt.value)                       //   sets the PMT value
j=cint(setres.value)                       //   sets the resolution value
k=cint(interval.value)                     //   sets the time interval between scans
```

| Algorithm |
|---|

```
n=cint(snumber.value)           // sets the number of scans
s=cstr(ipath.value)             // sets the path of the images
Scanner.PixelSize=j
Scanner.PMT(0)=i
t1=timer( )                     // sets the time 0
GenePix.DataScan                // starts the first scan
end sub
// Saves the image and launches a new scan
++++++++++++++++++++++++++++++++++++++++++++++++++++++++++++++++++++++
++++++++++++++++++++++++++++++++++++++++++++++++++++++
Function ScanDone( )            // STEP 4
if saved.checked=true then      //   saves the image
GenePix.SaveImages "C:\" & s & "\RT-"& cstr(formatnumber(timer( )-t1-k,0)) &" s.tif", "",
&h008000;
end if
GenePix.DiscardImages( )        // reinitializes the display
c=c+1                           // counts the number of scans
if c<n then                     // STEP5: and if necessary,
GenePix.DataScan                // launches a new scan
end if
End Function
</script>
<script language="JavaScript">
// This function is called after a scan is done
++++++++++++++++++++++++++++++++++++++++++++++++++++++++++++++++++++++
++++++++++++++++++++++++++++++++++++++++++++++++++++++
function waitjs( )              // STEP3
{
if c<n then                     //  if more scans have to be done,
setTimeout("ScanDone( )",k*1000); //  pauses the program during the time
else                            //  interval and calls the ScanDone function
End if
}
// Javascript callback: defines which function has to be run after which event
++++++++++++++++++++++++++++++++++++++++++++++++++++++++++++++++++++++
++++++++++++++++++++++++++++++++++++++++++++++++++++++
function InitializeCallbacks( )
{
GenePix.OnScanDone  = function ( ) { waitjs( ); }
}
</script>
</body>
</html>
```

FIG. 1 represents one embodiment of the invention in which parts of the two processes are present in the same compartment. The two processes are performed in the integrated system as long as the technical parts (necessary for having the specifications) are compatible with each other. The light source (1) is directed on the surface of the support (15) opposite to the surface in contact with the thermostatized carrier (12). The controller (11) includes a temperature controlling device.

In preferred embodiment, the excitation light (2) reaches the micro-array surface within an angle comprised between 45° and 135°, preferably between 60° and 120°, even more preferably between 80° and 100°. The light excitation is a direct excitation of the labelled target and do not use the internal reflection of the light such as provided by the evanescent waves.

In a preferred embodiment, the apparatus contains a substrate on which are fixed the capture molecules. In a preferred embodiment the support of the apparatus is thermostable and the surface is maintained flat at a temperature higher than 85° C. and even higher than 94° C. The support also presents a low self-fluorescence in order to be compatible fluorescence measurement. Preferably, the micro-array contained in the apparatus comprises more than 5 different capture molecules (20), preferably more than 20 and even more than 50.

In a preferred embodiment, the heating and cooling of the thermal cycler is performed at a ramping of 5° C. and better 30° C. per min. In a preferred embodiment, the localized area comprising the capture molecule is comprised between about 10 µm$^2$ and about 1 mm$^2$ and preferably between about 1 µm$^2$ and about 100 µm$^2$.

The apparatus further comprises an optical system for directing and focusing an excitation light (2) from said excitation light source (1) directly on said support, wherein the excitation light reaches the micro-array surface within an angle comprised between 45 and 135°.

In a specific embodiment a diagnostic kit is provided for monitoring on a micro-array a PCR amplification of a nucleotide molecule being present in a solution. The kit includes a cartridge comprising: a support (15) having fixed upon its surface a micro-array, comprising at least one capture molecule (20) being immobilized in specifically localized areas (21) of said support wherein the surface of said support is maintained flat at temperature higher than 85° C. and wherein said support have a low self-fluorescence, and a reaction chamber comprising 2 or even better 3 parts being in fluid connection to each other comprising a flat surface carrying the micro-array.

The diagnostic kit according to the invention also better comprises dNTPs, a thermostable DNA polymerase, buffer and optionally primers and/or a nucleotide molecule being used as an internal standard.

One example of the present invention applicable to the determination of the measurement of amplified targets from an original nucleotide molecule is presented here after.

EXAMPLE 1

Monitoring PCR Amplification on Micro-Array

Capture Nucleotide Sequence Immobilisation

The Diaglass slides (Eppendorf, Hamburg, Germany) are functionalized for the presence of aldehydes according to the method described in patent application WO02/18288. The protocol described in this patent application was followed for the grafting of aminated DNA to aldehyde derivatised glass. The aminated capture nucleotide sequences were spotted from solutions at concentrations of 3 µM. The capture nucleotide sequences were printed onto microscopic glass slides with a home made robotic device using 250 µm diameter pins. The spots have 400 µm in diameter and the volume dispensed is about 0.5 nl. Slides were dried at room temperature and stored at 4° C. until used.

The capture probes used in this experiment have the following sequences:

```
TP35S (SEQ ID NO: 1):
5'Amine-GTCATCCCTTACGTCAGTGGAGATAT-3'

TGUT (PCR control) (SEQ ID NO: 2):
5'Amine-GGGACTGGCTGCTATTGGGCGAA-3'

TPAT1 (SEQ ID NO: 3):
5'Amine-CTGTGTATCCCAAAGCCTCATGCaa-3'
```

Each capture probe comprises a spacer of 95 base long at its 5' end which has the following sequence:

```
                                        (SEQ ID NO: 4)
ATAAAAAAGTGGGTCTTAGAAATAAATTTCGAAGTGCAATAATTATTAT
TCACAACATTTCGATTTTTGCAACTACTTCAGTTCACTCCAAATTA.
```

PCR and Hybridization

PCR is designed for the amplification of the 35 promoter element of DNA sample of a genetically modified organism (GMO) Bt11 from reference flour ERM-BF412f.

The primers used in this experiment have the following sequences:

```
OP35SF (SEQ ID NO: 5):
5'-Cy3-CGTCTTCAAAGCAAGTGGATTG-3'

OP35SR (SEQ ID NO: 6):
5'-TCTTGCGAAGGATAGTGGGATT-3'
```

The amplified product has part of one of its strand sequence specific of capture molecules P35S (SEQ ID NO: 13).

A mix for PCR reaction is prepared as follows: for a final volume of 100 µl, we mix 10 µl of PCR eppendorf buffer, 10 µl of dNTP mix (each of dNTP at a final concentration of 200 µM), 1 µl of 20 µM primer OP35SF-Cy3 labelled at 5' end and 1 µl of 20 µM primer OP35SR, 2 µl of Eppendorf Taq DNA polymerase, 10 µl of NaCl 600 mM, 55 µl of water and 10 µl of 20 ng/µl of DNA sample extracted from reference flour ERM-BF412f.

25 µl of this PCR mix solution is loaded on the micro-array framed by an hybridization chamber, of 9×9 mm sealed with a smooth plastic coverslip (Grace Biolabs).

On the backside of the slide, we fix a special thermocouple which is temperature controlled. The complete heating process test bench is composed of the following relevant components: "thermocouple": RS-COMPONENT no. 219-4321 Self adhesive thermocouple Type K-Nickel Chromium/Nickel Aluminium, "transmitter": RS-COMPONENT no. 363-0222 Transmitter temperature thermocouple 4-20 mA, "converter": NATIONAL INSTRUMENTS 779026-01 USB-6009 48 Ksamples./sec DAQ multifonctions 14 bits for USB, "heater": MINCO Heating thermofoil flexible heater: Kapton 0.75"×0.75" HK 5578 R 18.3 L12F.

The thermocouple, sticks as close as possible of the spot to heat, measures the temperature thought the transmitter. This temperature information is given to a computer via the converter. Every 0.1 second, the software compares the temperature measured to the temperature set point requested by the final user and the controller adjusted the heating in order to provide the requested temperature.

The slide is then entered upside down into the Axon scanner (4100 personal) where it remains during the whole experiment. Scanned is performed with the channel Cy3 at a gain of 500 with a resolution of 10 micrometer.

The heating cover is then heated to 95° C. (denaturation) for 1 min then going to 56° C. (annealing) for 2 min and then for 1 min at 72° C. (elongation). The same cycle was repeated 39 times. The fluorescent light emission is determined by scanning the micro-array surface starting 1 min after the beginning of the annealing step (at 56° C.) of the cycles 6, 10, 14, 18, 22, 24, 26, 28, 30, 32, 33, 34, 35, 37, 38 and 40. The scanner uses as excitation light a laser which was focussed on the surface of the support. The emission light is detected and amplified by a photomultiplier. After image acquisition, the scanned 16-bit images were imported to the software, "Genepix 5" (Axon, Union city, Calif., USA) which was used to quantify the signal intensities. The signal was quantified on two capture probes P35S (SEQ ID NO: 1) and pat1 (SEQ ID NO: 2) present in six replicates on the array. The local background was subtracted and signal minus background is plotted against the number of cycles. The arrays also contained capture probes for negative hybridization control and positive detection control labeled with Cy3 present in quadruplicate on the array.

Result of the real-time PCR on micro-array is presented in FIG. 4. The result shows the appearance of a signal on the specific capture probe P35S at cycle 22. The signal continues to increase regularly until cycle 40. There is no signal observed on capture probe pat1.

The invention claimed is:

1. A method for monitoring on a micro-array a PCR amplification of a nucleotide molecule being present in a solution comprising the steps of:
providing a support having fixed upon its surface a micro-array comprising at least one capture molecule immobilized in specifically localized area(s) of said support and a reaction chamber,
introducing a solution containing said nucleotide molecule into said reaction chamber and reagents for nucleotide molecule amplification and labeling,
submitting the solution to at least five thermal cycles having at least 2 different temperature steps for denaturation, annealing and elongation in order to obtain labelled target nucleotide molecule by PCR amplification,
measuring the labelled target nucleotide molecule during at least five thermal cycles of the PCR amplification in the following way:
incubating said labelled target nucleotide molecule under conditions allowing a specific binding between said target nucleotide molecule and its corresponding capture molecule,
measuring light emission from the bound, labelled target nucleotide molecule in response to excitation light with said solution being present in the chamber and containing the labeled target nucleotide molecule, wherein the surface of emission for a localized area is between about 0.1 $\mu m^2$ and about 75 $mm^2$, and wherein said measurement is performed in real time during annealing and/or elongation steps of the at least five thermal cycles of the PCR amplification, and
processing data obtained in the at least five thermal cycles of the PCR amplification in order to detect and/or quantify an amount of nucleotide molecule present in the solution during PCR amplification.

2. The method of claim 1, wherein the light emission is measured at a defined timing from the beginning of a temperature step.

3. The method of claim 1, wherein the light emission is measured at within 5 min after the beginning of the annealing temperature step.

4. The method of claim 1, wherein the light emission is measured at the end of at least one of the temperature steps used for the PCR amplification.

5. The method of claim 1, wherein the data are processed in order to obtain a signal value for each of the localized area.

6. The method of claim 1, wherein the data are processed in order to obtain a signal value for each of the localized area and for the local background.

7. The method of claim 6, wherein the data are further processed by subtracting the background from the signal value for each of the localized area.

8. The method of claim 1, wherein the quantification of the amount of nucleotide molecule is performed by comparing the signal value of the localized area with a fixed value.

9. The method of claim 1, wherein the quantification of the amount of nucleotide molecule is performed by comparing the number of thermal cycles necessary to reach a fixed value (CT) with the CT of a reference nucleotide molecule.

10. The method of claim 9, wherein the reference nucleotide molecule is amplified in the same solution and detected on the same micro-array as the target nucleotide molecule.

11. The method of claim 1, wherein the quantification of the amount of nucleotide molecule is performed by comparing the number of thermal cycles necessary to reach a fixed value (CT) with a standard curve wherein the CT are plotted against standard concentrations.

12. The method of claim 1, wherein the reagents for nucleotide molecule amplification comprise a primer pair, dNTPs, a thermostable DNA polymerase and buffer.

13. The method of claim 1, wherein the reagents for nucleotide molecule amplification comprise a primer and/or dNTP labelled with a fluorescent dye.

14. The method of claim 1, wherein two fluorescent dyes are used in the same solution.

15. The method of claim 1, wherein the solution composition is adapted for performing the annealing of the primers on the nucleotide molecule and the specific binding of the labelled target molecule on the capture molecule during the same temperature step.

16. The method of claim 1, wherein the capture molecules bound to the labelled target nucleotide molecules are elongated during the temperature step of elongation.

17. The method of claim 16, wherein the capture molecules elongated are detected during the temperature step of denaturation.

18. The method of claim 1, wherein the localized area is comprised between about 10 $\mu m^2$ and about 1 $mm^2$.

19. The method of claim 1, wherein the micro-array comprises more than 5 different capture molecules.

20. The method of claim 1, wherein between 1 and 4 nucleotide molecules present in a solution are amplified and detected and/or quantified in the same assay.

21. The method of claim 1 wherein between 20 and 1000 nucleotide molecules present in a solution are amplified and detected and/or quantified in the same assay.

22. The method of claim 1, wherein the support contains a substrate on which are fixed the capture molecules.

23. The method of claim 1, wherein the support bears several micro-arrays separated by physical boundaries.

24. The method of claim 23, wherein the support has a multi-well plate or strip format.

25. The method of claim 24, wherein the multi-well plate is submitted to a temperature gradient during the measurement of light emission.

26. The method of claim 1, wherein an excitation light from a light source is directed on the surface of the support.

27. The method of claim 1, wherein a thermal cycle is performed within 10 min.

28. The method of claim 1, wherein 30 thermal cycles are performed within 5 h.

29. The method of claim 1, wherein the capture molecule is a single stranded polynucleotide containing a sequence able to specifically bind the labelled target nucleotide molecule and a spacer of at least 20 nucleotides.

30. The method of claim 13, wherein the fluorescent dye is selected from the group consisting of Cyanin 3, Cyanin 5 and Cyanin 7.

31. The method of claim 1, wherein the at least five thermal cycles have at least 3 different temperature steps for denaturation, annealing and elongation.

* * * * *

SEQUENCE LISTING

<160> NUMBER OF SEQ ID NOS: 6

<210> SEQ ID NO 1
<211> LENGTH: 26
<212> TYPE: DNA

```
<213> ORGANISM: Artificial Sequence
<220> FEATURE:
<223> OTHER INFORMATION: oligonucleotide probe

<400> SEQUENCE: 1
gtcatccctt acgtcagtgg agatat                                              26

<210> SEQ ID NO 2
<211> LENGTH: 23
<212> TYPE: DNA
<213> ORGANISM: Artificial Sequence
<220> FEATURE:
<223> OTHER INFORMATION: oligonucleotide probe

<400> SEQUENCE: 2
gggactggct gctattgggc gaa                                                 23

<210> SEQ ID NO 3
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 3
ctgtgtatcc caaagcctca tgcaa                                               25

<210> SEQ ID NO 4
<211> LENGTH: 95
<212> TYPE: DNA
<213> ORGANISM: Artificial Sequence
<220> FEATURE:
<223> OTHER INFORMATION: oligonucleotide probe

<400> SEQUENCE: 4
ataaaaaagt gggtcttaga aataaatttc gaagtgcaat aattattatt cacaacattt         60
cgatttttgc aactacttca gttcactcca aatta                                   95

<210> SEQ ID NO 5
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 5
cgtcttcaaa gcaagtggat tg                                                  22

<210> SEQ ID NO 6
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 6
tcttgcgaag gatagtggga tt                                                  22
```